United States Patent
Nikolskiy et al.

(10) Patent No.: US 11,562,547 B2
(45) Date of Patent: Jan. 24, 2023

(54) DIGITAL BLOCK OUT OF DIGITAL PREPARATION

(71) Applicant: James R. Glidewell Dental Ceramics, Inc., Newport Beach, CA (US)

(72) Inventors: Sergey Nikolskiy, Coto de Caza, CA (US); Fedor Chelnokov, Khimki (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 16/804,444

(22) Filed: Feb. 28, 2020

(65) Prior Publication Data

US 2021/0272377 A1  Sep. 2, 2021

(51) Int. Cl.
*G06T 19/20* (2011.01)
*G06T 7/00* (2017.01)
*G06T 7/64* (2017.01)
*A61C 13/00* (2006.01)

(52) U.S. Cl.
CPC .......... *G06T 19/20* (2013.01); *A61C 13/0004* (2013.01); *G06T 7/0012* (2013.01); *G06T 7/64* (2017.01); *G06T 2200/24* (2013.01); *G06T 2207/30036* (2013.01); *G06T 2210/41* (2013.01); *G06T 2219/2021* (2013.01)

(58) Field of Classification Search
CPC .......... G06T 19/20; G06T 7/0012; G06T 7/64; G06T 2200/24; G06T 2207/30036; G06T 2210/41; G06T 2219/2021; A61C 13/0004

See application file for complete search history.

(56) References Cited

U.S. PATENT DOCUMENTS

| | | | |
|---|---|---|---|
| 8,359,114 B2 | 1/2013 | Steingart et al. | |
| 9,168,114 B2 | 10/2015 | Jung et al. | |
| 9,622,835 B2 | 4/2017 | See et al. | |
| 2005/0177266 A1* | 8/2005 | Kopelman | A61C 5/77 700/117 |
| 2008/0261165 A1 | 10/2008 | Steingart et al. | |
| 2009/0248184 A1* | 10/2009 | Steingart | G06F 3/016 700/98 |
| 2011/0086328 A1 | 4/2011 | Wedeking | |
| 2012/0308963 A1* | 12/2012 | Hasselgren | A61C 8/0036 433/201.1 |
| 2013/0179126 A1* | 7/2013 | Meier | A61C 5/77 703/1 |

(Continued)

FOREIGN PATENT DOCUMENTS

| | | |
|---|---|---|
| EP | 2482754 A1 | 8/2012 |
| EP | 3547952 A1 | 10/2019 |

(Continued)

OTHER PUBLICATIONS

Arvind Shenoy et al., Periodontal considerations determining the design and location of margins in restorative dentistry, Journal of Interdisciplinary Dentistry, Jan.-Apr. 2012, vol. 2, Issue-1, downloaded from http://www.jidonline.com on Feb. 8, 2014, IP: 117.211.92.84 in 9 pages.

(Continued)

*Primary Examiner* — Michelle Chin
(74) *Attorney, Agent, or Firm* — Charles Fowler

(57) ABSTRACT

A system and method include performing digital block-out of one or more digital preparation teeth.

18 Claims, 15 Drawing Sheets

(56) References Cited

U.S. PATENT DOCUMENTS

| | | | |
|---|---|---|---|
| 2013/0226534 A1* | 8/2013 | Fisker | G06F 30/00 703/1 |
| 2014/0277665 A1* | 9/2014 | Fisker | G06F 30/00 700/98 |
| 2014/0335470 A1* | 11/2014 | Fisker | B29C 64/386 433/29 |
| 2018/0132982 A1 | 5/2018 | Nikolskiy et al. | |
| 2018/0153648 A1 | 6/2018 | Shanjani et al. | |

FOREIGN PATENT DOCUMENTS

| | | |
|---|---|---|
| EP | 3569167 A1 | 11/2019 |
| WO | 2015176004 A1 | 11/2015 |
| WO | 2016102451 A1 | 6/2016 |
| WO | 2018026966 A1 | 2/2018 |

OTHER PUBLICATIONS

Hong-Tzong Yau et al., Computer-aided Framework Design for Digital Dentistry, Computer-Aided Design and Applications, 5(5)m 2008, pp. 667-675.

J. Andreas Baerentzen and Henrik Aanaes, Member, IEEE, Signed Distance Computation Using the Angle Weighted Pseudonormal, IEEE Transactions on Visualization and Computer Graphics, vol. 11, No. 3, May/Jun. 2005, downloaded from orbit.dtu.dk on Feb. 19, 2020, in 12 pages.

\* cited by examiner

DIGITAL BLOCK OUT OF DIGITAL PREPARATION

BACKGROUND

Specialized dental laboratories typically use computer-aided design (CAD) and computer-aided manufacturing (CAM) milling systems to manufacture dental prostheses based on patient-specific instructions provided by dentists.

In a typical work flow, the dental laboratories receive information about a patient's oral situation from a dentist. Using this information, the dental laboratory designs a digital dental prosthesis such as a dental restoration on the CAD system and manufactures the dental restoration on the CAM system with a mill or other fabrication system. To use the CAD/CAM system, a digital model of the patient's dentition can be used as an input to the process. In the case of a dental restoration such as a crown, for example, the digital preparation tooth for the dental crown can have concavities on its surface. The dental restoration typically generated from a digital preparation tooth has an inner side (cavity) whose surface mirrors the preparation tooth surface and can therefore have bumps in regions of concavities of the preparation tooth surface. This can make manufacturing of the dental restoration more difficult and time consuming. For example, milling of the dental restoration can be more time consuming since the mill will reproduce each concavity on the preparation tooth as a bump on the inner side of the dental restoration. In some cases, undercut regions on the preparation tooth can also complicate crown fabrication and placement.

SUMMARY

A computer-implemented method of performing a digital block-out of one or more digital preparation teeth includes: receiving a digital model comprising one or more digital preparation teeth, determining one or more concave digital surface regions on the one or more digital preparation teeth, and reducing concavity of the one or more concave digital surface regions.

A system for performing a digital block-out of one or more digital preparation teeth, includes a processor, a computer-readable storage medium comprising instructions executable by the processor to perform steps including: receiving a digital model comprising one or more digital preparation teeth, determining one or more concave digital surface regions on the one or more digital preparation teeth, and reducing concavity of the one or more concave digital surface regions.

A method of performing a digital block-out of one or more digital preparation teeth includes: loading a digital model comprising one or more digital preparation teeth, and initiating concavity reduction of the one or more digital preparation teeth.

A non-transitory computer readable medium storing executable computer program instructions for performing a digital block-out of one or more digital preparation teeth, the computer program instructions including instructions for: receiving a digital model comprising one or more digital preparation teeth, determining one or more concave digital surface regions on the one or more digital preparation teeth, and reducing concavity of the one or more concave digital surface regions.

DETAILED DESCRIPTION

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

Figure 1:
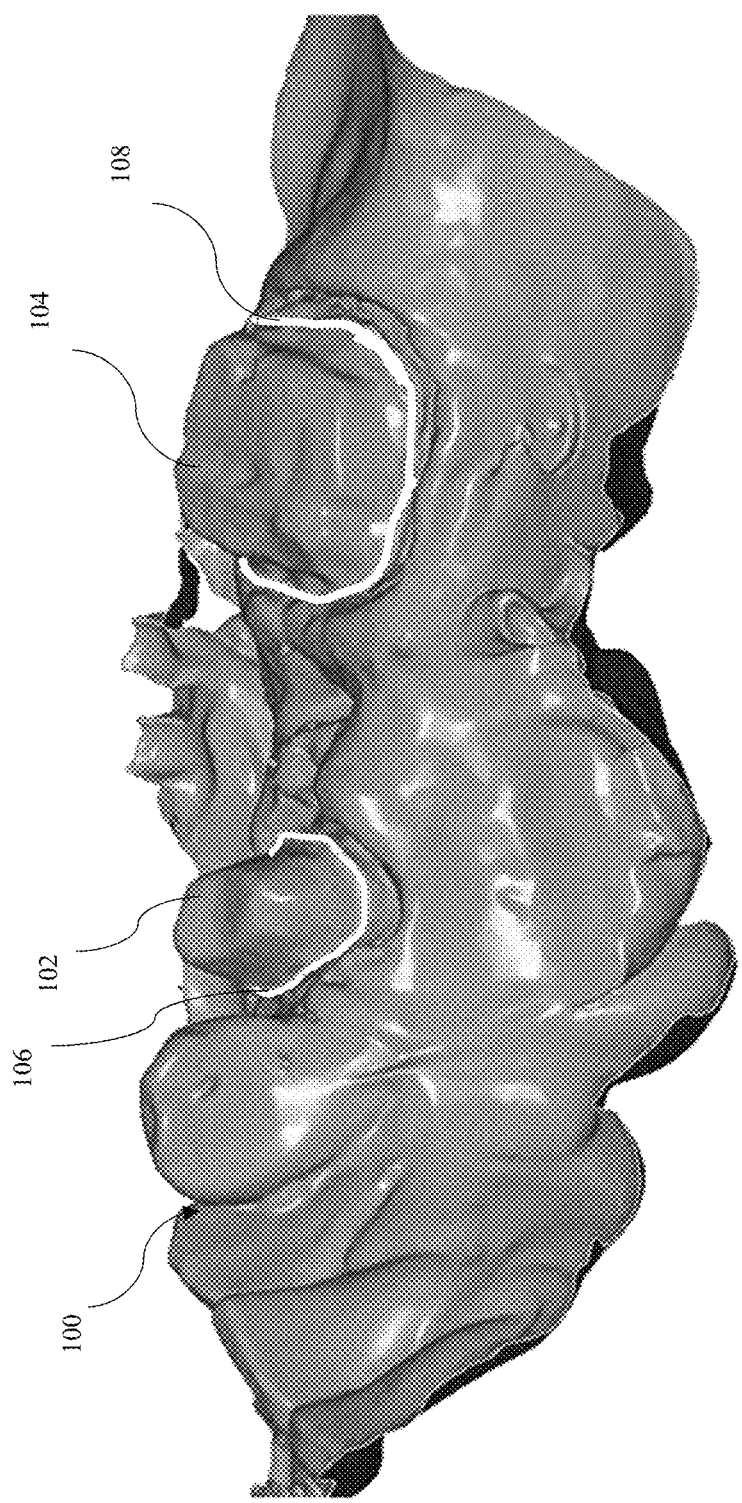
FIG. 1 is a perspective view of a digital model having digital preparation teeth.

FIG. 1 illustrates one example of a digital model 100 that can be generated by scanning a physical impression using any scanning technique known in the art including, but not limited to, for example, optical scanning, CT scanning, etc. The digital model 100 can also be generated by intraoral scanning of the patient's dentition, for example. One example is described in U.S. Patent Application No. US20180132982A1 to Nikolskiy et al., which is hereby incorporated in its entirety by reference. A conventional scanner typically captures the shape of the physical impression/patient's dentition in 3 dimensions during a scan and digitizes the shape into a 3 dimensional digital model. The digital model 100 can include multiple interconnected polygons in a topology that corresponds to the shape of the physical impression/patient's dentition, for example. In some embodiments, the polygons can include two or more digital triangles. In some embodiments, the scanning process can produce STL, PLY, or CTM files, for example that can be suitable for use with a dental restoration design software, such as FastDesign™ dental design software provided by Glidewell Laboratories of Newport Beach, Calif.

In some embodiments, the computer-implemented method can include, for example, receiving a digital model including one or more digital preparation teeth, determining one or more concave digital surface regions on the one or more digital preparation teeth, and reducing concavity of the one or more concave digital surface regions.

FIG. 1 illustrates an example in some embodiments of performing a digital block-out of one or more digital preparation teeth. In some embodiments, the digital block-out can be of a digital preparation tooth whose surface interfaces with any dental restoration cavity such as crowns, bridges, inlays/onlays, etc. for example. The computer-implemented method can receive a digital model 100 having one or more digital preparation teeth. The digital preparation teeth can be prepared, for example, by a user such as a dentist or dental technician, for example using dental restoration design software such as FastDesign™ or other design software known in the art in some embodiments. In some embodiments, the computer-implemented method can receive the digital model 100 that can include a first digital prepared tooth 102 and a second digital prepared tooth 104 and their corresponding margin lines, first digital prepared tooth margin line 106 and second digital prepared tooth margin line 108, respectively, for example. The first digital prepared tooth margin line 106 and second digital prepared tooth margin line 108 can be established using any technique known in the art. For example, in some embodiments, a technician (user) can manually mark the margin line using an input device such as a mouse or touch screen while viewing the digital model 100 on a display. Another technique to determine one or more digital preparation teeth with their corresponding margin line can be found in U.S. patent application Ser. No. 16/778,406 of Nikolskiy et al., titled SEMI-AUTOMATIC TOOTH SEGMENTATION, the entirety of which is hereby incorporated by reference. Another technique to determine digital preparation teeth and their corresponding margin line is described in, for example, *Computer-aided Framework Design for Digital Dentistry* by Hong-Tzong Yau, Chien-Yu Hsu, Hui-Lang Peng and Chih-Chuan Pai in Computer-Aided Design & Applications, 5(5), 2008, 667-675, the entirety of which is hereby incorporated by reference. Other techniques known in the art to specify digital preparation teeth and their corresponding margin line can be used.

More or fewer digital preparation teeth can be present in the digital model 100 in some embodiments, and the computer-implemented method can reduce concavity of one or more concave regions in each digital prepared tooth in the model. The digital teeth can be prepared to receive a dental restoration. In some embodiments, the dental restoration can be a crown, for example.

Figure 2:
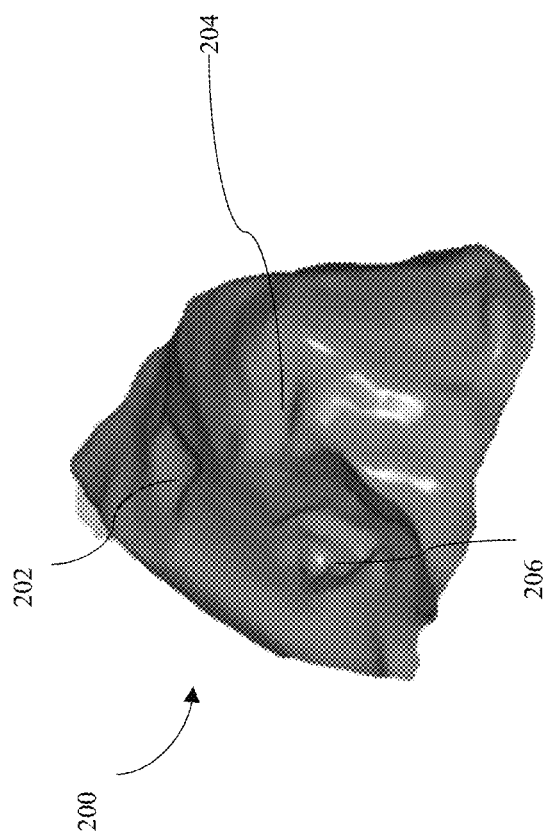
FIG. 2 is a perspective view of a single digital prepared tooth.

FIG. 2, illustrates one example of a single digital prepared tooth 200 that can be part of a digital model. The remaining portion of the digital model is not shown for clarity. The digital prepared tooth 200 can include, for example, one or more concave digital surface regions. For example, the digital prepared tooth 200 can include a first concave digital surface region 202, a second concave digital surface region 204, and a third concave digital surface region 206. More or fewer concave digital surface regions can be present on a digital prepared tooth such as digital prepared tooth 200 in some embodiments, for example.

Figure 3:
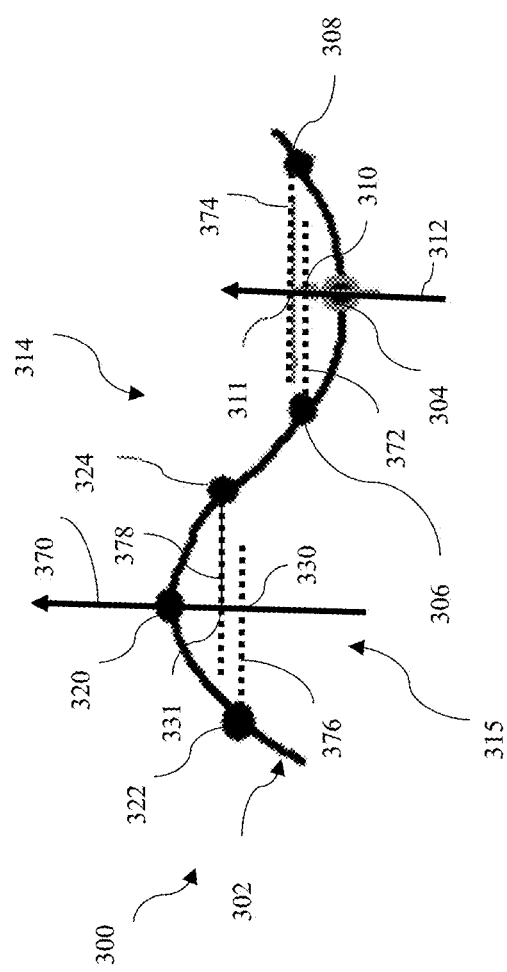
FIG. 3 is a 2 dimensional cross section illustration of a portion of a digital prepared tooth showing determining maximum vertex position.

In some embodiments, the computer-implemented method can determine one or more concave digital surface regions on the one or more digital preparation teeth. FIG. 3 illustrates one example of a digital prepared tooth 300 surface region 302. The digital surface region 302 is shown in a two dimensional cross section for clarity. It is understood that the digital surface region is a 3 dimensional digital surface. In some embodiments, the computer-implemented method can determine a concave surface region based on positions of neighboring vertices of a given vertex. In some embodiments, the position is along a normal of the given vertex. In some embodiments, the computer-implemented method can determine a normal for each vertex using techniques known in the art. One example of determining a normal for each vertex can be found in Bærentzen, J. A., & Aanæs, H. (2005). *Signed Distance Computation Using The Angle Weighted Pseudonormal. IEEE Transactions on Visualization and Computer Graphics*, 11(3), 243-253, the entirety of which is hereby incorporated by reference. For example, in some embodiments, the computer-implemented method can determine a given vertex normal by computing the unit normal for each triangular face around the given vertex and computing the vertex normal as the weighted sum of face normal with the weight equal to an incident angle as follows:

$$n_\alpha = \frac{\sum_i \alpha_i \, n_i}{\left\| \sum_i \alpha_i \, n_i \right\|}$$

where the normal is n, i runs over the faces incident with x and $\alpha_i$ is the incident angle. Another technique to determine a given vertex normal known in the art can include computing face normal as described previously and then compute the given vertex normal as the weighted sum of face normal with the weight equal to the area of the face, for example.

In some embodiments, the computer-implemented method can determine neighboring vertex positions and determine a maximum position vertex from one or more neighboring vertices of the given vertex. The computer-implemented method can determine a neighboring vertex position by calculating its projected position on a normal of the given vertex. For example, the computer-implemented method can project a line from a neighboring vertex to the normal of the given vertex so that the projected line intersects the normal of the given vertex at 90 degrees. The computer-implemented method can determine a neighbor's position as the intersection point of the neighbor vertex's projected line with the normal of the given vertex. In some embodiments, the computer-implemented method can determine the maximum position vertex based on the position of each neighboring vertex's position on the normal of the given vertex. For example, in some embodiments, neighboring positions positioned toward the direction of the normal (higher up on the normal) can have a higher position value than those positioned further away from the direction of the normal (lower on the normal). In some embodiments, the computer-implemented method can determine the maximum position vertex as the neighboring vertex position with the highest value.

In some embodiments, the number of neighboring vertices evaluated can be two to six neighboring vertices (inclusive), for example. In some embodiments, the number of neighboring vertices can be greater than six. In some embodiments, the number of neighboring vertices to be evaluated can be a user-configurable value.

In some embodiments, the computer-implemented method can determine whether the given vertex is in a locally concave surface region or a locally convex surface region based on the maximum position vertex. For example, in some embodiments, if the maximum position vertex is positioned above the given vertex along its normal (e.g. closer to the normal direction than the given vertex), then the computer-implemented method can determine that the given vertex is in a locally concave region. If, on the other hand, the maximum position vertex is positioned below the given vertex along its normal (e.g. further away from the normal direction than the given vertex), then the computer-implemented method can determine that the given vertex is in a locally convex region. If the maximum position vertex is positioned at the given vertex along its normal, then the computer-implemented method can determine that the given vertex is in a locally non-concave digital surface region.

For example, as illustrated in FIG. 3, given vertex 304 has a first neighbor vertex 306 and a second neighbor vertex 308. The computer-implemented method can determine a first neighbor vertex position 310 of the first neighbor vertex 306 by projecting a first neighbor vertex line 372 from the first neighbor vertex 306 to the given vertex normal 312 at 90 degrees to the given vertex normal 312. Similarly, the computer-implemented method can determine a second neighbor vertex position 311 of the second neighbor vertex 308 by projecting a second neighbor vertex line 374 from the second neighbor vertex 308 to the given vertex normal 312 at 90 degrees to the given vertex normal 312. In this example, the computer-implemented method can determine second vertex position 311 as the maximum position vertex since the second vertex position 311 is above the first vertex position 310 in the direction of the given vertex normal 312. Since the maximum position vertex 311 is positioned above (or on the outer digital surface 314 region of) the given vertex 304 along its normal 312, the computer-implemented method can in some embodiments determine that the given vertex 304 is in a concave region.

As another example, given convex vertex 320 has a first convex neighbor vertex 322 and a second convex neighbor vertex 324. The computer-implemented method can determine a first convex neighbor vertex position 330 of the first convex neighbor vertex 322 by projecting a first convex neighbor vertex line 376 from the first convex neighbor vertex 322 to the given convex vertex normal 370 at 90 degrees to the given convex vertex 320. Similarly, the computer-implemented method can determine a second convex neighbor vertex position 331 of the second convex neighbor vertex 324 by projecting a second convex neighbor vertex line 378 from the second convex neighbor vertex 324 to the given convex vertex 320 at 90 degrees to the given convex vertex 320. In this example, the computer-implemented method can determine second convex neighbor vertex position 331 as the maximum position vertex since the second convex neighbor vertex position 331 is above the first convex neighbor vertex position 330 in the direction of the given convex vertex 320. Since the maximum position vertex 331 is positioned below (or on the inner digital surface 315 region of) the given convex vertex 320 along its normal 370, the computer-implemented method can in some embodiments determine that the given convex vertex 320 is in a convex region. The computer-implemented method can, in some embodiments, evaluate every vertex in this manner to identify one or more concave digital surface regions.

Figure 4:
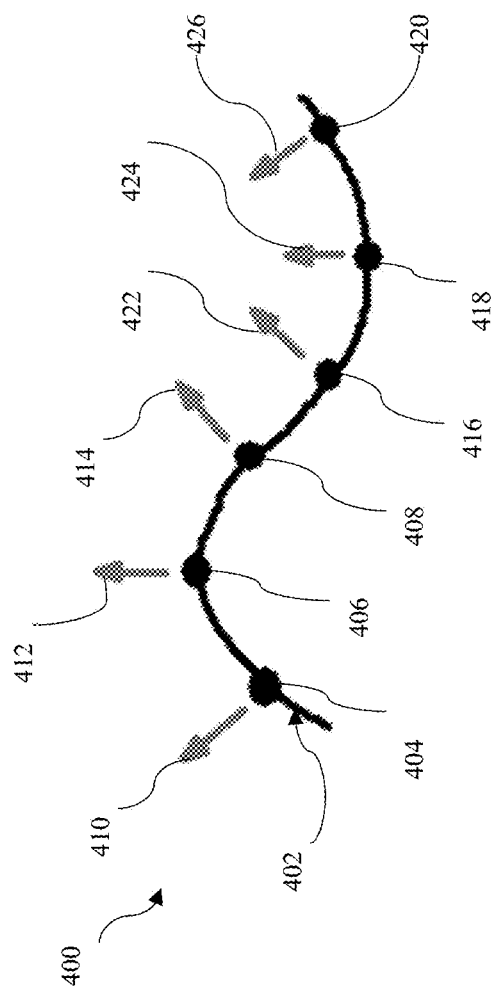
FIG. 4 is a 2 dimensional cross section illustration of a portion of a digital prepared tooth showing digital surface vertices and their corresponding normals.

In some embodiments, the computer-implemented method can evaluate and classify every digital surface vertex as locally concave or locally convex or non-concave. FIG. 4 illustrates one example of a digital prepared tooth 400 surface region 402. The digital surface region 402 is shown in a two dimensional cross section for clarity. It is understood that the digital surface region is a 3 dimensional digital surface. Using the techniques described with respect to FIG. 3 and in this disclosure, the computer-implemented method can determine first vertex 404, second vertex 406, a third vertex 408 with first vertex normal 410, second vertex normal 412, and third vertex normal 414, respectively, as convex vertices. The computer-implemented method can determine a fourth vertex 416, a fifth vertex 418, and a sixth vertex 420 having fourth vertex normal 422, fifth vertex normal 424, and sixth vertex normal 426, respectively, as concave vertices. The number of vertices shown in the figure is for illustrative purposes only; more or fewer vertices can be present in the digital model.

Figure 5:
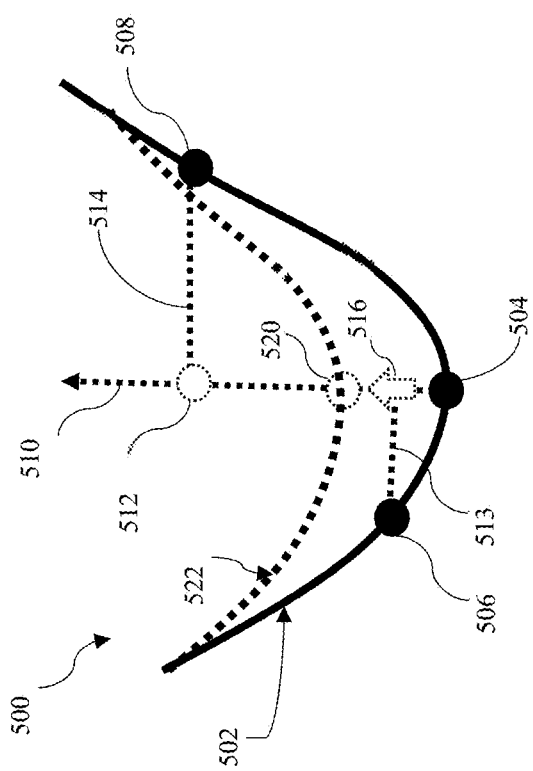
FIG. 5 is a 2 dimensional cross section illustration of a portion of a digital prepared tooth showing determining the maximum vertex position.

In some embodiments, the computer-implemented method can reduce concavity of the one or more concave digital surface regions. For example, in some embodiments, the computer-implemented method can reduce concavity of one or more concave vertices. In some embodiments, reducing concavity can include moving one or more vertices by a distance away from the digital surface. The computer-implemented method can thus push out the vertices and the one or more concave digital surface regions to reduce their concavity. In some embodiments, the computer-implemented method can reduce concavity of one or more concave regions based on a user-configurable value. For example, the distance can be proportionate to a user-configurable value. The computer-implemented method can receive the user-configurable value from a configuration file, for example. In some embodiments, the computer-implemented method can keep one or more locally convex regions intact. In some embodiments, the computer-implemented method can determine the distance based on a first and second neighbor vertex position. For example, the computer-implemented method can in some embodiments reduce concavity of one or more concave digital surface regions by moving one or more locally concave vertices along their respective normal(s) toward a maximum position vertex of its immediate neighbors. For example, in some embodiments, the computer-implemented method can determine the distance based on a first and second neighbor vertex position. In some embodiments, the computer-implemented method can move one or more locally concave vertices in the direction of their respective normal(s). In some embodiments, the computer-implemented method determines new positions of one or more vertices along their normals before moving the one or more vertices. FIG. 5 illustrates a portion of a concave digital surface region 500 shown in a two dimensional cross section for clarity. It is understood that the digital surface region is a 3 dimensional digital surface. FIG. 5 includes an initial concave digital surface 502 with a given vertex 504. The given vertex 504 can have a first neighbor vertex 506, a second neighbor vertex 508, and a given vertex normal 510 determined as described previously in the present disclosure, for example.

The computer-implemented method can determine a maximum position vertex 512 from a second neighbor vertex projection line 514 projected on to the given vertex normal 510 as described previously in the present disclosure, for example, since a projection line 513 from the first neighbor vertex 506 is lower or further away from the direction of the given vertex normal 510 than the second neighbor vertex projection line 514. In some embodiments, the computer-implemented method can determine a new given vertex position as the maximum position vertex 512. In some embodiments, the computer-implemented method can determine a new given vertex position anywhere in a direction 516 toward the maximum position vertex 512 along the given vertex normal 510, for example.

In some embodiments, the computer-implemented method can determine the new given vertex position based on a user-configurable intensity value. For example, the computer-implemented method can receive an intensity value, which can be loaded from a configuration file, for example, or set by a user using an input device, for example. In some embodiments, the user-configurable intensity value can determine how close to the maximum position vertex the new given vertex position will be positioned. For example, the user-configurable intensity value can be a percentage or proportion of distance to the maximum position vertex 512 in a direction 516 along the given vertex normal 510. Accordingly, in some embodiments, the computer-implemented can determine the new given vertex position based on a user-configurable percentage of the total distance to the maximum position vertex 512 from the given vertex 504. For example, in some embodiments, the computer-implemented method can determine a new given vertex position 520 that is along the given vertex normal 510. In some embodiments, the computer-implemented method can determine the new given vertex position as the maximum position vertex 512, for example. As a further example, if the intensity value is set to, for example, 1, or 100%, then the computer-implemented method can determine the new given vertex position as the maximum position vertex 512. However, if the intensity value is set to ½ or a value less than 1 or 100%, then the computer-implemented method can determine the new given vertex position as ½ the distance to the maximum position vertex 512 along the given vertex normal 510, for example. In some embodiments, the computer-implemented method can move the given vertex 504 to the new given vertex position such as new given vertex position 520, thus creating a reduced concavity digital surface region 522 with less concavity than the initial concave digital surface 502, for example.

Figure 6A:
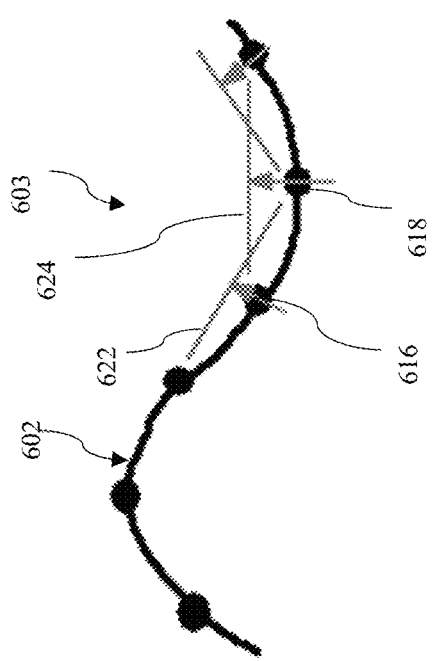
FIG. 6(A) is a 2 dimensional cross section illustration of a portion of a digital prepared tooth showing vertex normals and their corresponding maximum vertex position.

In some embodiments, the computer-implemented method can determine all new vertex positions from initial concave digital surface region vertices before moving each initial concave digital surface region vertex to its corresponding determined new vertex position as described previously, for example. For example, FIG. 6A illustrates an initial digital surface 602 shown in a two dimensional cross section for clarity. It is understood that the initial concave digital surface region is a 3 dimensional digital surface. The computer-implemented method can determine an initial concave region 603 as described previously that includes a first initial vertex 616 and a second initial vertex 618. The computer-implemented method can determine a maximum position corresponding to each initial vertex as described previously. For example, the computer-implemented method can determine a first maximum position 622 and a second maximum position 624 corresponding to the first initial vertex 616 and the second initial vertex 618, respectively.

Figure 6B:
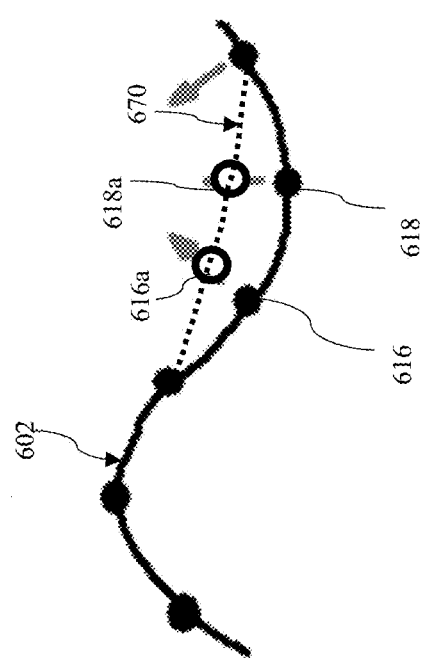
FIG. 6(B) is a 2 dimensional cross section illustration of a portion of a digital prepared tooth showing new vertex positions.

The computer-implemented can, in some embodiments, determine new vertex positions of the initial vertices before moving the initial vertices. In some embodiments, the new vertex position can be between the initial vertex and its corresponding maximum position vertex or at the maximum position vertex as described previously, for example. In some embodiments, the new vertex position can be at the maximum position as described previously, for example. FIG. 6(B) illustrates an example in some embodiments in which the computer-implemented method determines new vertex positions such as first new vertex position 616a and second new vertex position 618a, corresponding to first initial vertex 616 and second initial vertex 618 prior to moving the initial vertices, for example. Once the computer-implemented determines the new vertex positions of all new vertices, the computer-implemented method can move the initial vertices to their corresponding new vertex positions. The computer-implemented method can determine the new vertex positions as described previously, for example. After the computer-implemented method moves the first initial vertex 616 and a second initial vertex 618 to the first new vertex position 616a and the second new vertex position 618a, respectively, the new vertices can form a reduced concavity digital surface 670, for example.

In some embodiments, the computer implemented method can reduce concavity in one or more concave regions by repeating the concave reduction process as described by a user configurable number of iterations. For example, in some embodiments, the computer-implemented method can receive the number of iterations. The computer-implemented method can in each iteration as described previously determine a normal of each vertex, determine a maximum position vertex of each vertex, determine one or more concave region vertices, determine a corresponding new vertex of each concave vertex, and move each concave vertex to its corresponding new vertex position. The computer-implemented method can in one or more subsequent iterations repeat the process. In some embodiments, the number of iterations can be 40 iterations, for example. More or fewer iterations can be applied in some embodiments. As more iterations are applied, the amount of concavity reduction in the one or more concave digital surface regions can increase.

Figure 7:
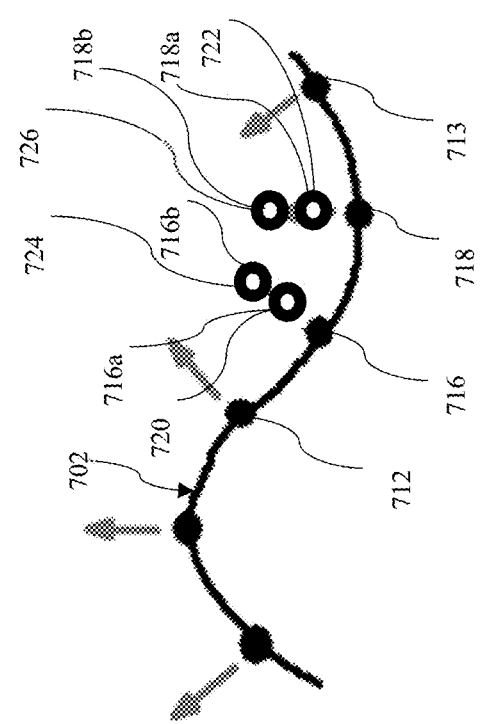
FIG. 7 is a 2 dimensional cross section illustration of a portion of a digital prepared tooth showing new vertex positions after first and second iterations.

FIG. 7 illustrates an example of applying two iterations of concavity reduction. The figure is an example only, and the computer-implemented method can apply one or more iterations. The figure includes an initial digital surface 702, which is shown in a two dimensional cross section for clarity. It is understood that the digital surface region is a 3 dimensional digital surface.

In a first iteration, the computer-implemented method can determine first concave vertex 716 and second concave vertex 718 as concave vertices described previously. The computer-implemented method can determine a first new vertex position 720 and second new vertex position 722 of the first concave vertex 716 and the second concave vertex 718, respectively, for example. The computer-implemented method can determine the first new vertex position 720 by comparing projection line positions of vertices neighboring the first concave vertex 716, such as vertex 712 and second concave vertex 718 in some embodiments, for example. The computer-implemented method can determine the second new vertex position 722 by comparing projection line positions of vertices neighboring the second concave vertex 718, such as first concave vertex 716 and vertex 713, for example. Both new vertices can be determined as described previously. For example, in some embodiments, the new vertex positions can be at their corresponding maximum position vertex. In some embodiments, the new vertex positions can be at a proportionate distance between the concave vertex and its corresponding maximum position vertex. In some embodiments, the computer-implemented method can move the first concave vertex 716 to the first new vertex position 720 as first concave vertex 716a and the second concave vertex 718 to the second new vertex position 722 as second concave vertex 718b, for example.

In a second iteration, the computer-implemented method can determine first concave vertex 716a and second concave vertex 718a as concave vertices as described previously in the present disclosure. The computer-implemented method can determine a third new vertex position 724 and fourth new vertex position 726 of the first concave vertex 716a and the second concave vertex 718a, respectively, for example. The computer-implemented method can determine the third new vertex position 724 by comparing projection line positions of vertices neighboring the first concave vertex 716a, such as vertex 712 and second concave vertex 718a in some embodiments, for example. The computer-implemented method can determine the fourth new vertex position 726 by comparing projection line positions of vertices neighboring the second concave vertex 718a, such as first concave vertex 716a and vertex 713, for example. Both new vertices can be determined as described previously. For example, in some embodiments, the new vertex positions can be at their corresponding maximum position vertex. In some embodiments, the new vertex positions can be at a proportionate distance between the concave vertex and its corresponding maximum position vertex. In some embodiments, the computer-implemented method can move the first concave vertex 716a to the third new vertex position 724 as first concave vertex 716b and the second concave vertex 718a to the fourth new vertex position 726 as second concave vertex 718b, for example. The reduced concave digital surface can in this example include first concave vertex 716b and second concave vertex 718b.

Figure 8:
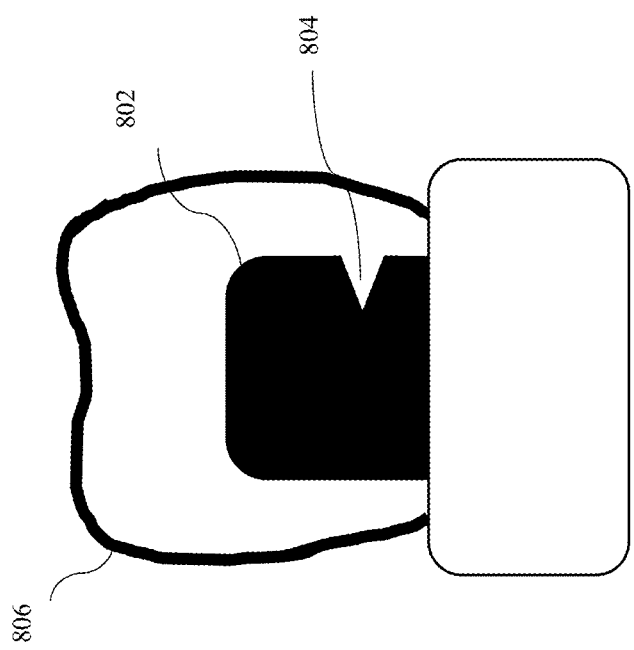
FIG. 8 is a 2 dimensional cross section illustration of a portion of a digital prepared tooth with an undercut region.

In some embodiments, the computer-implemented method can reduce one or more undercut regions. Undercut regions on a digital preparation tooth typically include regions of a high degree of concavity. FIG. 8 is an illustration of an example of a digital prepared tooth 802 having one or more undercut regions such as undercut region 804. As illustrated in the figure, the undercut region 804 on the digital preparation tooth 802 has a high degree of concavity. Placement of a crown 806 or other dental restoration can be challenging due to the high degree of concavity of the undercut region 804. In some embodiments, the computer-implemented method can digitally block out one or more undercut regions such as undercut region 804 by reducing concavity on the digital preparation tooth. In some embodiments, the computer-implemented method can completely digitally block out one or more undercut region(s) by iteratively reducing concavity of one or more digital teeth as described previously in the present disclosure.

Figure 9:
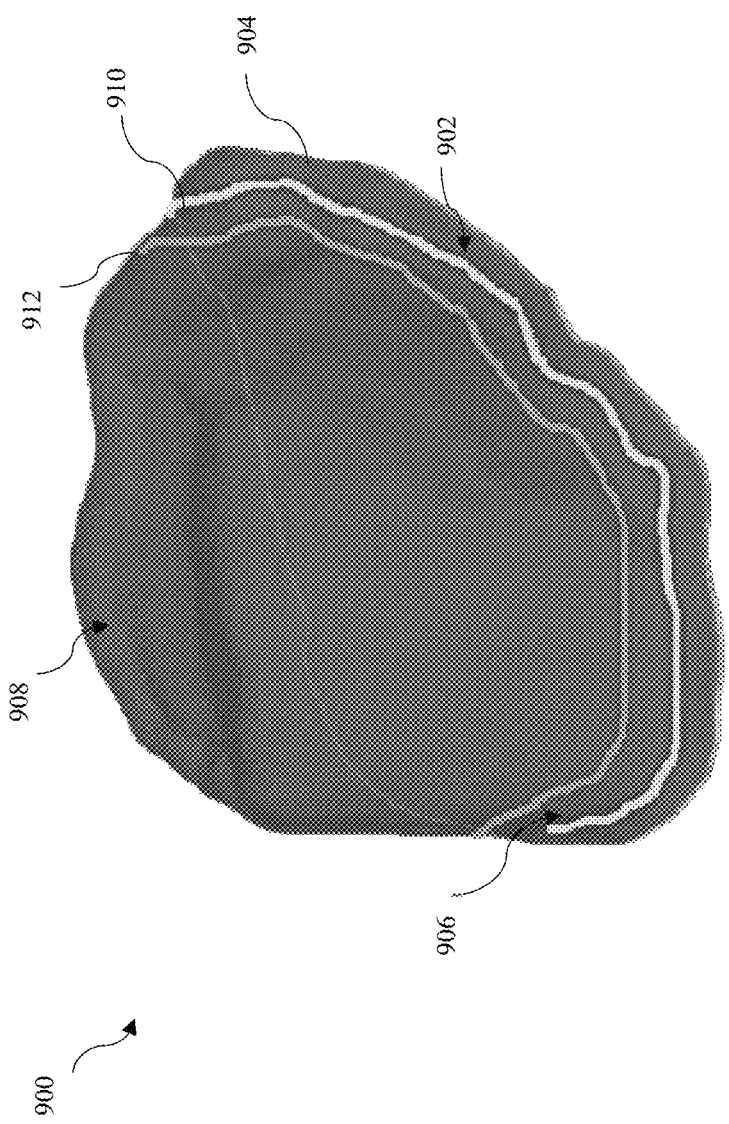
FIG. 9 is a perspective view of a digital model having different regions.

In some embodiments, the computer-implemented method can include reducing concavity based on a region of the digital tooth. For example, in some embodiments, the computer-implemented method can include reducing concavity in an inner region of a digital prepared tooth surface by an inner region amount and reducing concavity in a transition region of the digital prepared tooth surface by a transition region amount. In some embodiments, the transition region amount can be proportionate to a distance from a margin line of the digital prepared tooth, for example. In some embodiments, reducing concavity in a margin region can be skipped, for example. FIG. 9 illustrates an example of a digital prepared tooth 900 that includes a dead zone region 902 adjacent to a margin line 904, a transition region 906 adjacent to the dead zone region 902, and an inner region 908 adjacent to the transition region 906. The dead zone region 902 can have a dead zone boundary 910. In some embodiments, the dead zone boundary 910 can be a dead zone boundary distance $D_1$ from the margin line 904. In some embodiments, for example, the dead zone boundary distance can be a user-configurable value. In some embodiments, for example, the dead zone boundary distance $D_1$ can be, for example, 2 mm from the margin line 904. The transition region 906 can include a transition region boundary 912, for example. The transition region boundary 912 can separate the transition region 906 from the inner region 904, for example. In some embodiments, the transition region boundary can be a distance $D_2$ from the margin line 904 such that $D_2 > D_1$. For example, the transition region boundary 912 can be 2.5 mm from the margin line 904 in some embodiments.

In some embodiments, the computer-implemented method can determine concavity reduction based on the region of the digital prepared tooth as follows:

For every point on the digital surface inside the margin line compute the distance d along the digital surface to the margin line. If the distance d is less than $D_1$ then the point in question in within dead zone and intensity there is set to zero. If the distance d is greater than $D_2$ then the point in question in within inner area and intensity there is set to a user-configurable value such as 1, for example (that is the vertex is moved to the position of its maximum position vertex). If the distance d is in between $D_1$ and $D_2$ then the point in question is within the transition region, and the intensity there can be defined by a function smoothly connecting from 0 at $D_1$ to 1 at $D_2$. For example, let $y=(d-D_1)/(D_2-D_1)$, then the intensity can be $f=y^2*(3-2y)$. Other smoothing functions/values can be used.

In some embodiments determining one or more concave digital surface regions and reducing their concavity as described can performed automatically. For example, determining one or more concave digital surface regions and reducing their concavity can be performed without requiring a user to select specific regions in which to reduce concavity.

Figure 10A:
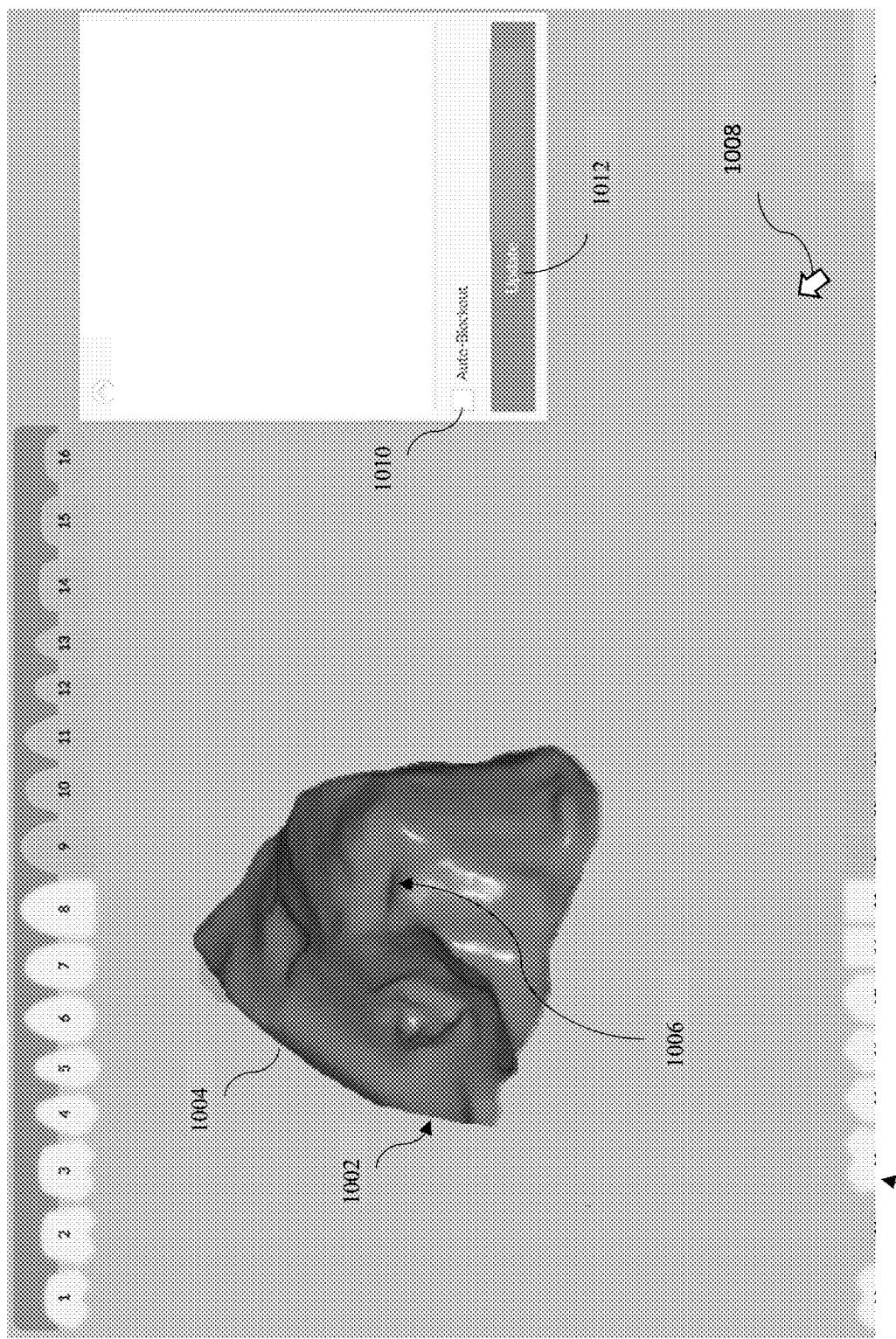
FIGS. 10(A) and 10(B) are illustrations of a Graphical User Interface showing a digital model and controls.
Figure 10B:
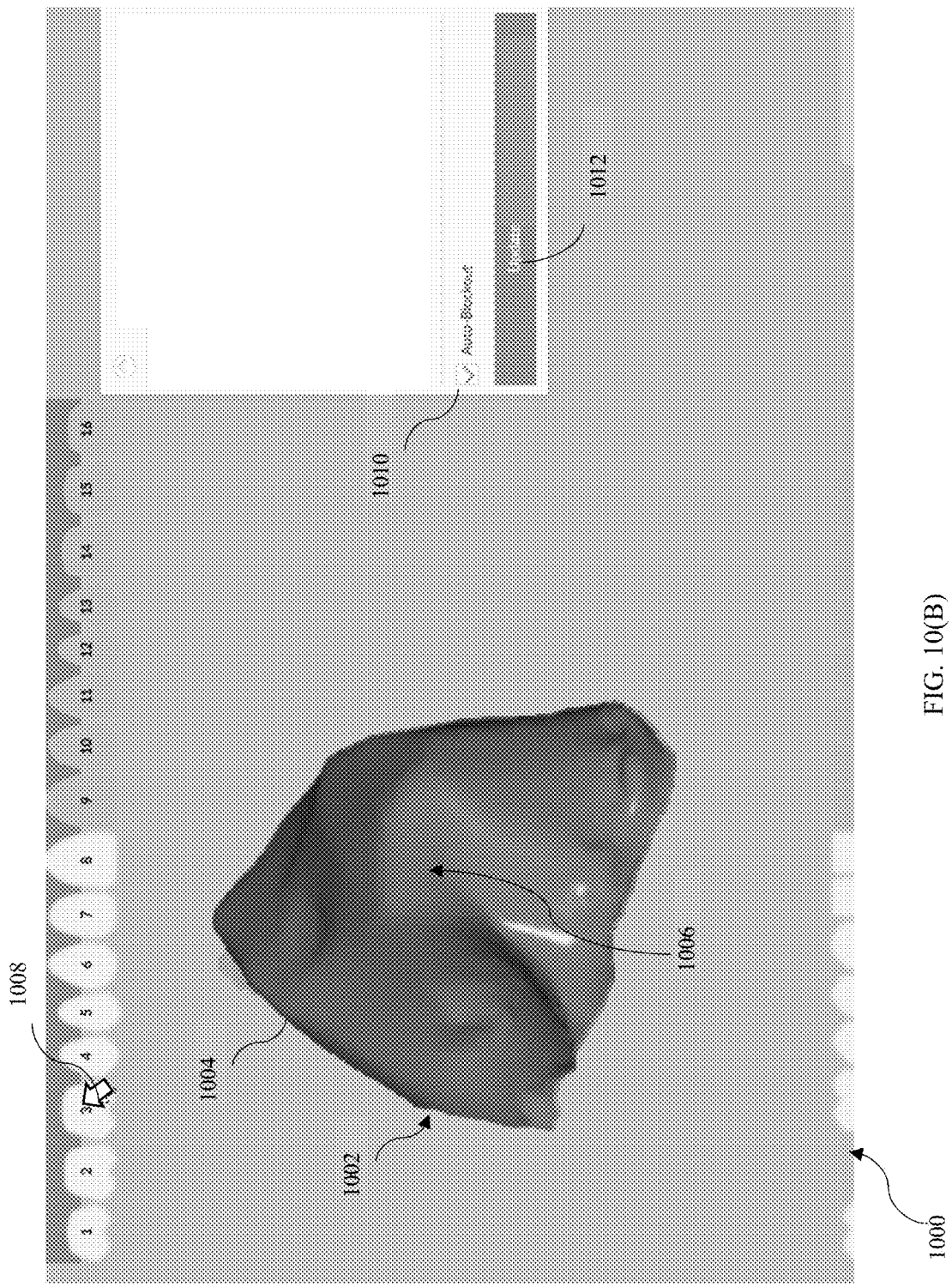

In some embodiments, a user can load onto a computer a digital model that includes one or more digital preparation teeth and initiate concavity reduction of the one or more digital preparation teeth as described in the present disclosure. For example, FIG. 10(A) illustrates Graphical User Interface (GUI) 1000 shown on a display with a digital prepared tooth 1002 which the user can load from a local file system, network, database, or other storage device known in the art. The digital prepared tooth 1002 can include a margin line 1004 and one or more concave regions 1006, for example. A user can, using an input device such as a mouse or a touch screen, manipulate pointer 1008 to select, for example, a GUI element such as a check box 1010 to automatically block out the digital prepared tooth 1002. After selecting the check box 1010, the user can initiate concavity reduction of the digital prepared tooth 1002 by, for example, selecting another GUI element such as button 1012, which in this example is an Update button. The computer-implemented method can perform block out using one or more features disclosed herein, for example. FIG. 10(B) illustrates the same digital model after block out has been performed. The one or more concave regions 1006 have reduced concavity. Although particular GUI features are shown, they are for illustrative purposes. Other GUI features known in the art can be used.

Any of the features described herein can be performed automatically by the computer-implemented method. Any user-configurable values can be received by the computer-implemented method. In some embodiments, the user-configurable values can be received from a local or networked file system. In some embodiments, the user-configurable values can be received from other computer-implemented programs or functions.

Figure 11:
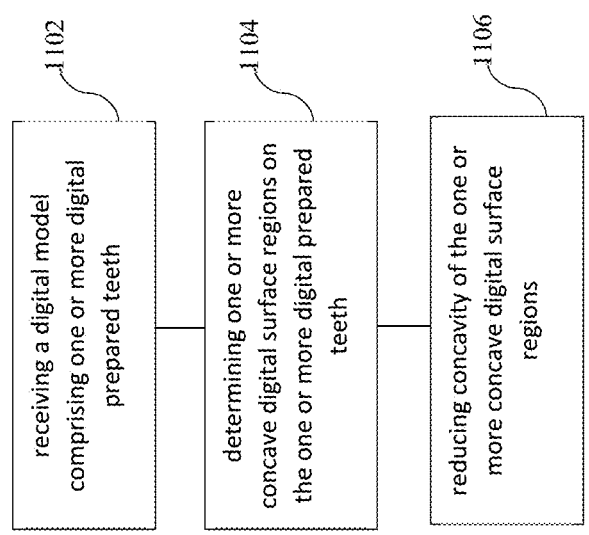
FIG. 11 is a flowchart of a method in some embodiments.

FIG. 11 illustrates one embodiment of a computer-implemented method of performing a digital block-out of one or more digital preparation teeth. The method can include, for example, receiving a digital model including one or more digital preparation teeth at 1102, determining one or more concave digital surface regions on the one or more digital preparation teeth at 1104, and reducing concavity of the one or more concave digital surface regions at 1106.

The method can include optional features. For example, any of the method steps can be performed automatically, including but not limited to, receiving a digital model including one or more digital preparation teeth at 1102, determining one or more concave digital surface regions on the one or more digital preparation teeth at 1104, and/or reducing concavity of the one or more concave digital surface regions at 1106. For example, the one or more concave digital surface regions can include an undercut region. Reducing concavity of one or more concave digital surface regions can include digitally blocking out the undercut region. The digital tooth can be prepared for a crown. Reducing concavity can include: reducing concavity in an inner region of a digital tooth surface by an inner region amount and reducing concavity in a transition region of the digital tooth surface by a transition region amount. The transition region amount can be proportionate to a distance from a margin line of the digital tooth. A margin region can be skipped. Reducing concavity can include moving one or more vertices by a distance away from the digital surface. Moving one or more vertices can be along a normal of the vertex. The computer-implemented method can determine the distance based on a first and second neighbor vertex position. The distance can be proportionate to a user-configurable value. An inner region amount and the transition region amount can include a user-configurable value. Determining one or more concave digital surface regions can be performed automatically.

Figure 12:
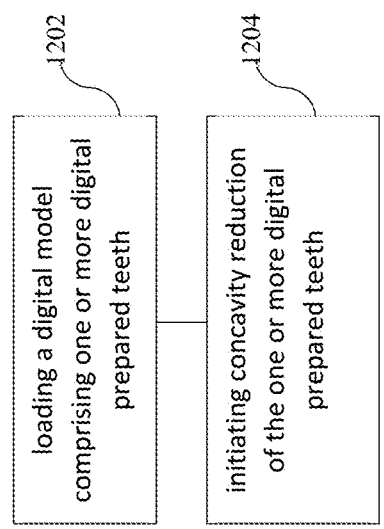
FIG. 12 is a flowchart of a method in some embodiments.

FIG. 12 illustrates a method of performing a digital block-out of one or more digital preparation teeth, including loading a digital model comprising one or more digital preparation teeth at 1202 and initiating concavity reduction of the one or more digital preparation teeth 1204. These steps can be performed by a user using a computer, for example.

The method can include optional features. For example, the concavity reduction can be performed automatically. Concavity reduction can include determining one or more concave digital surface regions on the one or more digital preparation teeth and reducing concavity of the one or more concave digital surface regions. These can be performed automatically by the computer, for example. The one or more concave digital surface regions can include an undercut region. Reducing concavity of one or more concave digital surface regions can include digitally blocking out the undercut region. The digital tooth can be prepared for a crown. Reducing concavity can include: reducing concavity in an inner region of a digital tooth surface by an inner region amount and reducing concavity in a transition region of the digital tooth surface by a transition region amount. The transition region amount can be proportionate to a distance from a margin line of the digital tooth. A margin region can be skipped. Reducing concavity can include moving one or more vertices by a distance away from the digital surface. Moving one or more vertices can be along a normal of the vertex. The computer-implemented method can determine the distance based on a first and second neighbor vertex position. The distance can be proportionate to a user-configurable value. An inner region amount and the transition region amount can include a user-configurable value. Determining one or more concave digital surface regions can be performed automatically.

Some embodiments include a non-transitory computer readable medium storing executable computer program instructions for performing a digital block-out of one or more digital preparation teeth, the computer program instructions including instructions for: loading a digital model with one or more digital preparation teeth, determining one or more concave digital surface regions on the one or more digital preparation teeth and reducing concavity of the one or more concave digital surface regions.

The instructions can include optional features. For example, the concavity reduction can be performed automatically. Concavity reduction can include determining one or more concave digital surface regions on the one or more digital preparation teeth and reducing concavity of the one or more concave digital surface regions. These can be performed automatically by the computer, for example. The one or more concave digital surface regions can include an undercut region. Reducing concavity of one or more concave digital surface regions can include digitally blocking out the undercut region. The digital tooth can be prepared for a crown. Reducing concavity can include: reducing concavity in an inner region of a digital tooth surface by an inner region amount and reducing concavity in a transition region of the digital tooth surface by a transition region amount. The transition region amount can be proportionate to a distance from a margin line of the digital tooth. A margin region can be skipped. Reducing concavity can include moving one or more vertices by a distance away from the digital surface. Moving one or more vertices can be along a normal of the vertex. The computer-implemented method can determine the distance based on a first and second neighbor vertex position. The distance can be proportionate to a user-configurable value. An inner region amount and the transition region amount can include a user-configurable value. Determining one or more concave digital surface regions can be performed automatically.

Figure 13:
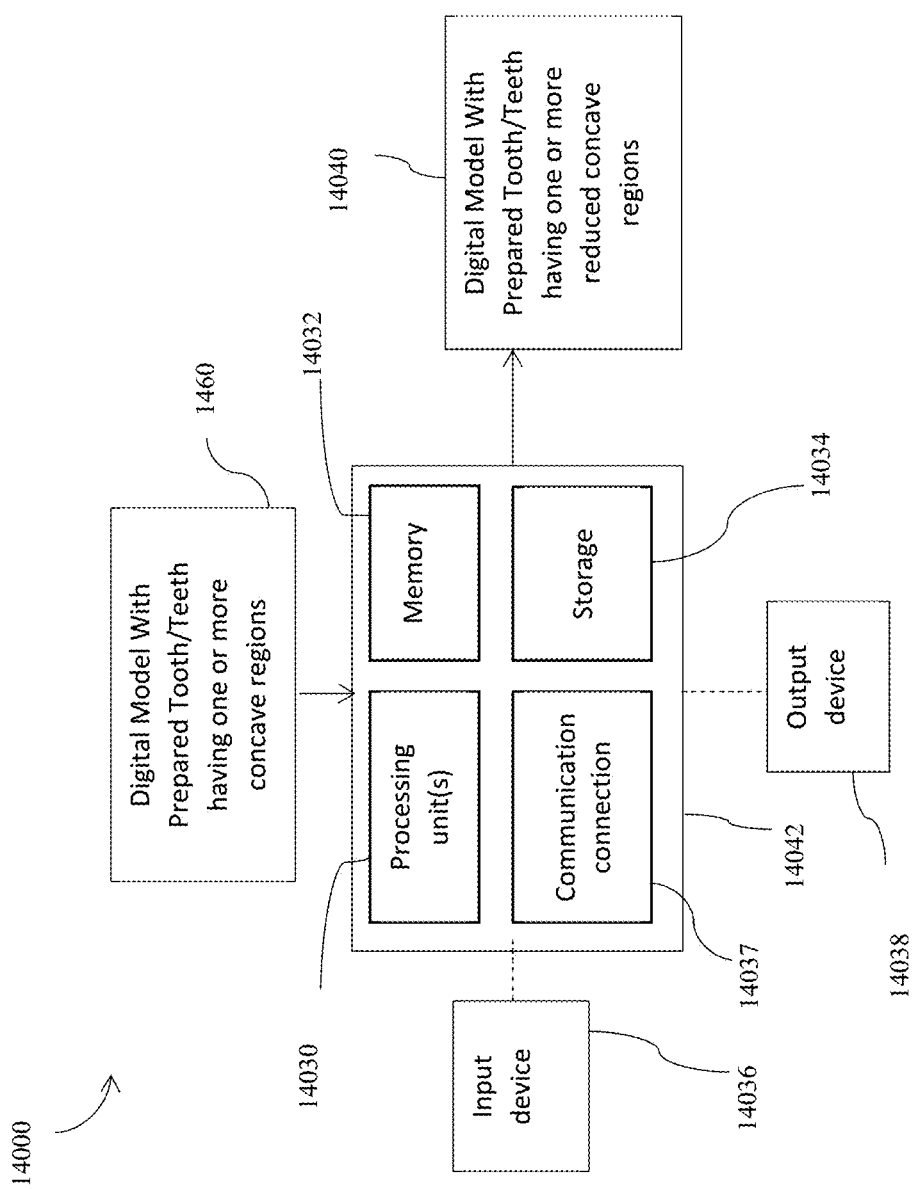
FIG. 13 is a system in some embodiments.

FIG. 13 illustrates a processing system 14000 in some embodiments. The system 14000 can include a processor 14030, computer-readable storage medium 14034 having instructions executable by the processor to perform one or more steps described in the present disclosure.

For example, some embodiments include a processing system 14000 for performing a digital block-out of one or more digital preparation teeth: a processor 14030, a computer-readable storage medium 14034 including instructions executable by the processor to perform steps including: receiving a digital model having one or more digital preparation teeth 1460, determining one or more concave digital surface regions on the one or more digital preparation teeth, and reducing concavity of the one or more concave digital surface regions. The system can provide a digital model with preparation tooth/teeth having one or more reduced concave regions 14040. The digital model with preparation tooth/teeth having one or more reduced concave regions can be used to generate a dental restoration, for example. For example, the digital model with preparation tooth/teeth having one or more reduced concave regions can be provided to a CAM system or other fabrication system that can mill the dental restoration.

The system can include optional features. For example, the concavity reduction can be performed automatically. Concavity reduction can include determining one or more concave digital surface regions on the one or more digital preparation teeth and reducing concavity of the one or more concave digital surface regions. These can be performed automatically by the computer, for example. The one or more concave digital surface regions can include an undercut region. Reducing concavity of one or more concave digital surface regions can include digitally blocking out the undercut region. The digital tooth can be prepared for a crown. Reducing concavity can include: reducing concavity in an inner region of a digital tooth surface by an inner region amount and reducing concavity in a transition region of the digital tooth surface by a transition region amount. The transition region amount can be proportionate to a distance from a margin line of the digital tooth. A margin region can be skipped. Reducing concavity can include moving one or more vertices by a distance away from the digital surface. Moving one or more vertices can be along a normal of the vertex. The computer-implemented method can determine the distance based on a first and second neighbor vertex position. The distance can be proportionate to a user-configurable value. An inner region amount and the transition region amount can include a user-configurable value. Determining one or more concave digital surface regions can be performed automatically.

One or more advantages of one or more features in the present disclosure can include, for example, simplifying crown milling by reducing or eliminating concavities from the digital preparation tooth which the mill would have to reproduce as bumps or elevations on the crown. One or more advantages of one or more features in the present disclosure can include, for example, automatically reducing or removing concavities on the digital preparation tooth surface before creating a crown, thereby improving time and simplicity of subsequent crown fabrication. One or more advantages of one or more features in the present disclosure can include, for example, reducing or eliminating undercut regions that can complicate crown fabrication and/or placement. One or more advantages of one or more features in the present disclosure can include, for example, reducing or removing small concavities while making large concavities less pronounced. One or more advantages of one or more features in the present disclosure can include, for example, reducing or removing concavities without modifying an area immediately adjacent to the margin line. One or more advantages of one or more features in the present disclosure can include, for example, easier manufacture of an inner cavity of the crown (or bridge) improve the chance that the crown can be inserted on top of the prepared tooth. One or more advantages of one or more features in the present disclosure can include, for example, more smooth surface of the prepared tooth, thereby simplifying any subsequent manufacturing. One or more advantages of one or more features in the present disclosure can include, for example, improved insertion by full or partial elimination of undercuts. One or more advantages of one or more features in the present disclosure can include, for example, not requiring user-input to manually define a region where to apply digital block out. For example, one or more concave regions can be determined by the computer-implemented method, and concavities can be found automatically. One or more advantages of one or more features in the present disclosure can include, for example, more precise determination and reduction of one or more concave regions on the digital preparation tooth. One or more advantages of one or more features in the present disclosure can include, for example, application to a region of any shape (e.g. whole tooth prepared for the crown except for a boundary strip).

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these features can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication medium. Such suitable communication medium include, for example, the Internet, the World Wide Web, an intranet, software applications, cable (including fiber optic cable), magnetic communications, electromagnetic communications (including RF, microwave, and infrared communications), electronic communications, or other such communication medium.

In view of the many possible embodiments to which the principles of the disclosure may be applied, it should be recognized that the illustrated embodiments are only examples and should not be taken as limiting the scope of the disclosure.

What is claimed is:

1. A computer-implemented method of performing a digital block-out of one or more digital preparation teeth, comprising:
    receiving a digital model comprising one or more digital preparation teeth;
    determining one or more concave digital surface regions on a surface of the one or more digital preparation teeth that interfaces with a dental restoration cavity; and
    reducing concavity of the one or more concave digital surface regions,
    wherein reducing concavity comprises moving one or more vertices of the one or more digital preparation teeth by a distance away from the digital surface,
    wherein moving the one or more vertices of the one or more digital preparation teeth by a distance away from the digital surface comprises pushing out the one or more vertices of the one or more digital preparation teeth to reduce the concavity of the one or more concave digital surface regions.

2. The method of claim 1, wherein the one or more concave digital surface regions comprise an undercut region.

3. The method of claim 2, wherein reducing concavity of one or more concave digital surface regions comprises digitally blocking out the undercut region.

4. The method of claim 1, wherein the digital tooth is prepared for a crown.

5. The method of claim 1, wherein reducing concavity comprises:
    reducing concavity in an inner region of a digital preparation tooth surface by an inner region amount; and
    reducing concavity in a transition region of the digital preparation tooth surface by a transition region amount.

6. The method of claim 5, wherein the transition region amount is proportionate to a distance from a margin line of the digital tooth.

7. The method of claim 1, further comprising a margin region wherein reducing concavity is skipped.

8. The method of claim 1, wherein moving one or more vertices comprises along a normal of the vertex.

9. The method of claim 1, wherein the computer-implemented method determines the distance based on a first and second neighbor vertex position.

10. The method of claim 9, wherein the distance is proportionate to a user-configurable value.

11. The method of claim 1, wherein an inner region amount and the transition region amount comprises a user-configurable value.

12. The method of claim 1, wherein determining one or more concave digital surface regions is performed automatically.

13. A system for performing a digital block-out of one or more digital preparation teeth, comprising:

a processor;

a computer-readable storage medium comprising instructions executable by the processor to perform steps comprising:

receiving a digital model comprising one or more digital preparation teeth;

determining one or more concave digital surface regions on a surface of the one or more digital preparation teeth that interfaces with a dental restoration cavity; and reducing concavity of the one or more concave digital surface regions, wherein reducing concavity comprises moving one or more vertices of the one or more digital preparation teeth by a distance away from the digital surface, wherein moving the one or more vertices of the one or more digital preparation teeth by a distance away from the digital surface comprises pushing out the one or more vertices of the one or more digital preparation teeth to reduce the concavity of the one or more concave digital surface regions.

14. The system of claim 13, wherein determining one or more concave digital surface regions is performed automatically.

15. A method of performing a digital block-out of one or more digital preparation teeth, comprising:

loading a digital model comprising one or more digital preparation teeth; and initiating concavity reduction of the one or more digital preparation teeth, wherein concavity reduction comprises determining one or more concave digital surface regions on a surface of the one or more digital preparation teeth that interfaces with a dental restoration cavity; and reducing concavity of the one or more concave digital surface regions, wherein reducing concavity comprises moving one or more vertices of the one or more digital preparation teeth by a distance away from the digital surface, wherein moving the one or more vertices of the one or more digital preparation teeth by a distance away from the digital surface comprises pushing out the one or more vertices of the one or more digital preparation teeth to reduce the concavity of the one or more concave digital surface regions.

16. The method of claim 15, wherein determining one or more concave digital surface regions is performed automatically.

17. A non-transitory computer readable medium storing executable computer program instructions for performing a digital block-out of one or more digital preparation teeth, comprising, the computer program instructions including instructions for:

receiving a digital model comprising one or more digital preparation teeth;

determining one or more concave digital surface regions on a surface of the one or more digital preparation teeth that interfaces with a dental restoration cavity; and reducing concavity of the one or more concave digital surface regions, wherein reducing concavity comprises moving one or more vertices of the one or more digital preparation teeth by a distance away from the digital surface, wherein moving the one or more vertices of the one or more digital preparation teeth by a distance away from the digital surface comprises pushing out the one or more vertices of the one or more digital preparation teeth to reduce the concavity of the one or more concave digital surface regions.

18. The non-transitory computer readable medium of claim 17, wherein reducing concavity is performed automatically.

* * * * *